US010036692B2

(12) United States Patent
Perley et al.

(10) Patent No.: US 10,036,692 B2
(45) Date of Patent: *Jul. 31, 2018

(54) SYSTEM AND METHOD FOR ESTIMATING ROTOR BLADE LOADS OF A WIND TURBINE

(71) Applicant: General Electric Company, Schenectady, NY (US)

(72) Inventors: Thomas Franklin Perley, Simpsonville, SC (US); Brandon Shane Gerber, Charleston, SC (US); Tim Robert Gerloff, Berlin (DE)

(73) Assignee: General Electric Company, Schenectady, NY (US)

( * ) Notice: Subject to any disclaimer, the term of this patent is extended or adjusted under 35 U.S.C. 154(b) by 547 days.

This patent is subject to a terminal disclaimer.

(21) Appl. No.: 14/540,275

(22) Filed: Nov. 13, 2014

(65) Prior Publication Data
US 2016/0138571 A1    May 19, 2016

(51) Int. Cl.
*F03D 7/02* (2006.01)
*G01N 3/24* (2006.01)
(Continued)

(52) U.S. Cl.
CPC ............... *G01N 3/24* (2013.01); *F03D 1/06* (2013.01); *F03D 7/043* (2013.01); *F03D 17/00* (2016.05);
(Continued)

(58) Field of Classification Search
CPC ......... B82Y 10/00; B82Y 30/00; B82Y 40/00; B82Y 15/00; H01L 51/0048;
(Continued)

(56) References Cited

U.S. PATENT DOCUMENTS

| 7,175,389 B2 | 2/2007 | Moroz |
| 7,281,891 B2 | 10/2007 | Smith et al. |

(Continued)

FOREIGN PATENT DOCUMENTS

WO    WO 2011/157271 A2    12/2011

OTHER PUBLICATIONS

Selvam, "Individual Pitch Control for Large Scale Wind Turbines", ECN-E-07-053, pp. 13-26, Jan. 1, 2007.
(Continued)

*Primary Examiner* — Robert Bachner
(74) *Attorney, Agent, or Firm* — Dority & Manning, P.A.

(57) ABSTRACT

The present subject matter is directed to a method for estimating rotor blade loads, e.g. a blade root resultant moment, of a wind turbine. In one embodiment, the method includes measuring, via one or more sensors, a plurality of operating parameters of the wind turbine. Another step includes estimating out-of-plane and in-plane forces acting on the rotor blade based at least partially on the plurality of operating parameters. Further, the method includes determining an application point for the out-of-plane and in-plane forces along a span of the rotor blade. A further step includes estimating out-of-plane and in-plane moments of the rotor blade based at least partially on the out-of-plane and in-plane forces and the respective application points. Thus, the method includes calculating the load acting on the rotor blade based at least partially on the out-of-plane and in-plane moments.

20 Claims, 9 Drawing Sheets

(51) Int. Cl.
*F03D 7/04* (2006.01)
*F03D 17/00* (2016.01)
*F03D 1/06* (2006.01)

(52) U.S. Cl.
CPC ... *F05B 2260/821* (2013.01); *F05B 2270/331* (2013.01); *Y02E 10/721* (2013.01); *Y02E 10/723* (2013.01)

(58) Field of Classification Search
CPC ....... H01L 2924/0002; H01L 27/11565; H01L 27/11582; H01L 27/283; H01L 2924/00; H01L 51/0508; H01L 51/0579; H01L 21/28282
See application file for complete search history.

(56) References Cited

U.S. PATENT DOCUMENTS

| | | | |
|---|---|---|---|
| 7,342,323 | B2 | 3/2008 | Avagliano et al. |
| 7,346,462 | B2 | 3/2008 | Delmerico |
| 7,351,033 | B2 | 4/2008 | McNerney |
| 7,476,485 | B2 | 1/2009 | Hatakeyama et al. |
| 7,505,833 | B2 | 3/2009 | Delmerico et al. |
| 7,573,149 | B2 | 8/2009 | Kammer et al. |
| 7,613,548 | B2 | 11/2009 | Cardinal et al. |
| 7,822,560 | B2 | 10/2010 | LeMieux |
| 7,861,583 | B2 | 1/2011 | Honhoff et al. |
| 7,942,629 | B2 | 5/2011 | Shi et al. |
| 7,964,979 | B2 | 6/2011 | Miranda et al. |
| 7,979,167 | B2 | 7/2011 | Delmerico et al. |
| 8,025,476 | B2 | 9/2011 | Zheng et al. |
| 8,050,887 | B2 | 11/2011 | Ahmann |
| 8,257,040 | B2 | 9/2012 | Chen et al. |
| 2010/0014969 | A1* | 1/2010 | Wilson .................. F03D 7/0224 416/1 |
| 2013/0033040 | A1 | 2/2013 | Bowyer et al. |
| 2013/0156577 | A1 | 6/2013 | Esbensen et al. |
| 2014/0271193 | A1* | 9/2014 | Baker .................... F03D 15/15 416/61 |

OTHER PUBLICATIONS

Leithead et al., "A Novel Approach to Structural Load Control Using Intelligent Actuators", 17th Mediterranean conference on IEEE Control and Automation, Piscataway, NJ, USA, pp. 1257-1262, Jun. 24, 2009.

Jelavic et al., "Individual Pitch Control of Wind Turbine Based on Loads Estimation", 34th Annual Conference of IEEE Industrial Electronics, Piscataway, NJ, USA, pp. 228-234, Nov. 10, 2008.

Friis et al., "Repetitive Model Predictive Approach to Individual Pitch Control of Wind Turbines", Proceedings of the 50th IEEE Conference on Decision and Control and European Control Conference, pp. 1-7, Jan. 1, 2011.

PCT Search Report and Written Opinion issued in connection with corresponding PCT Application No. PCT/US2015/059649 dated Jan. 26, 2016.

Related Application U.S. Appl. No. 13/970,930, filed Aug. 20, 2013.
Related U.S. Appl. No. 14/032,279, filed Sep. 20, 2013.

* cited by examiner

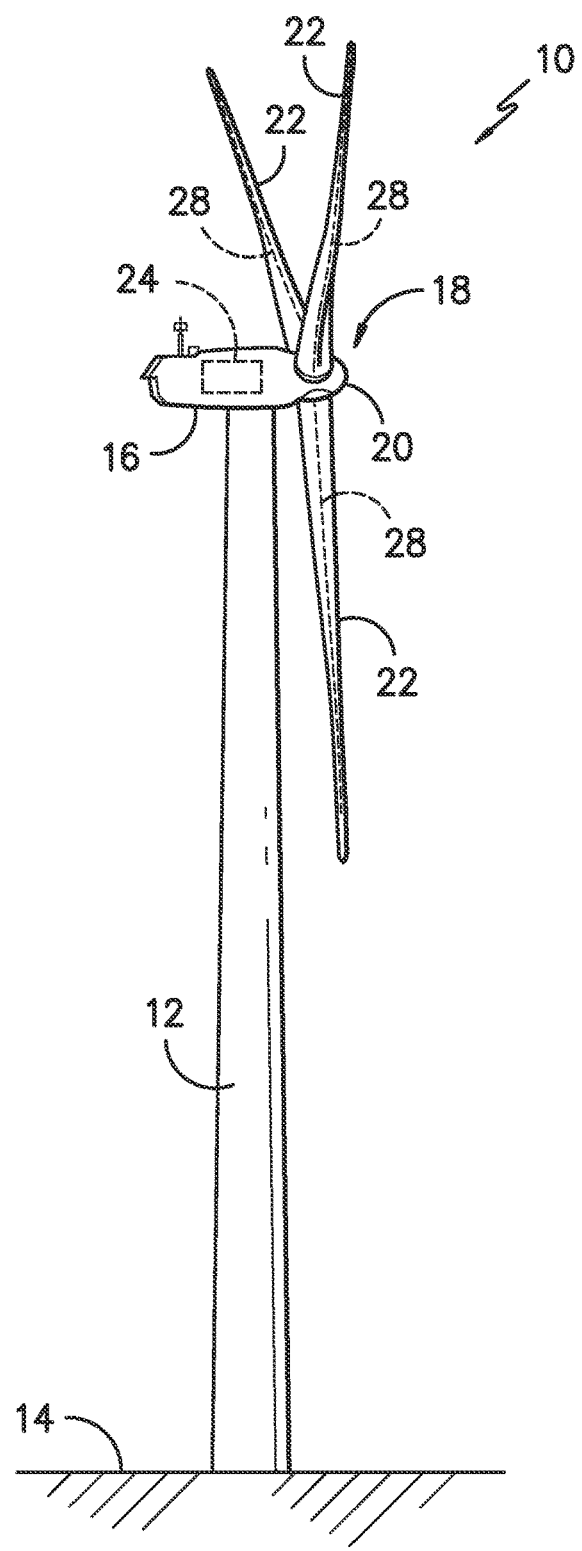
FIG. -1-

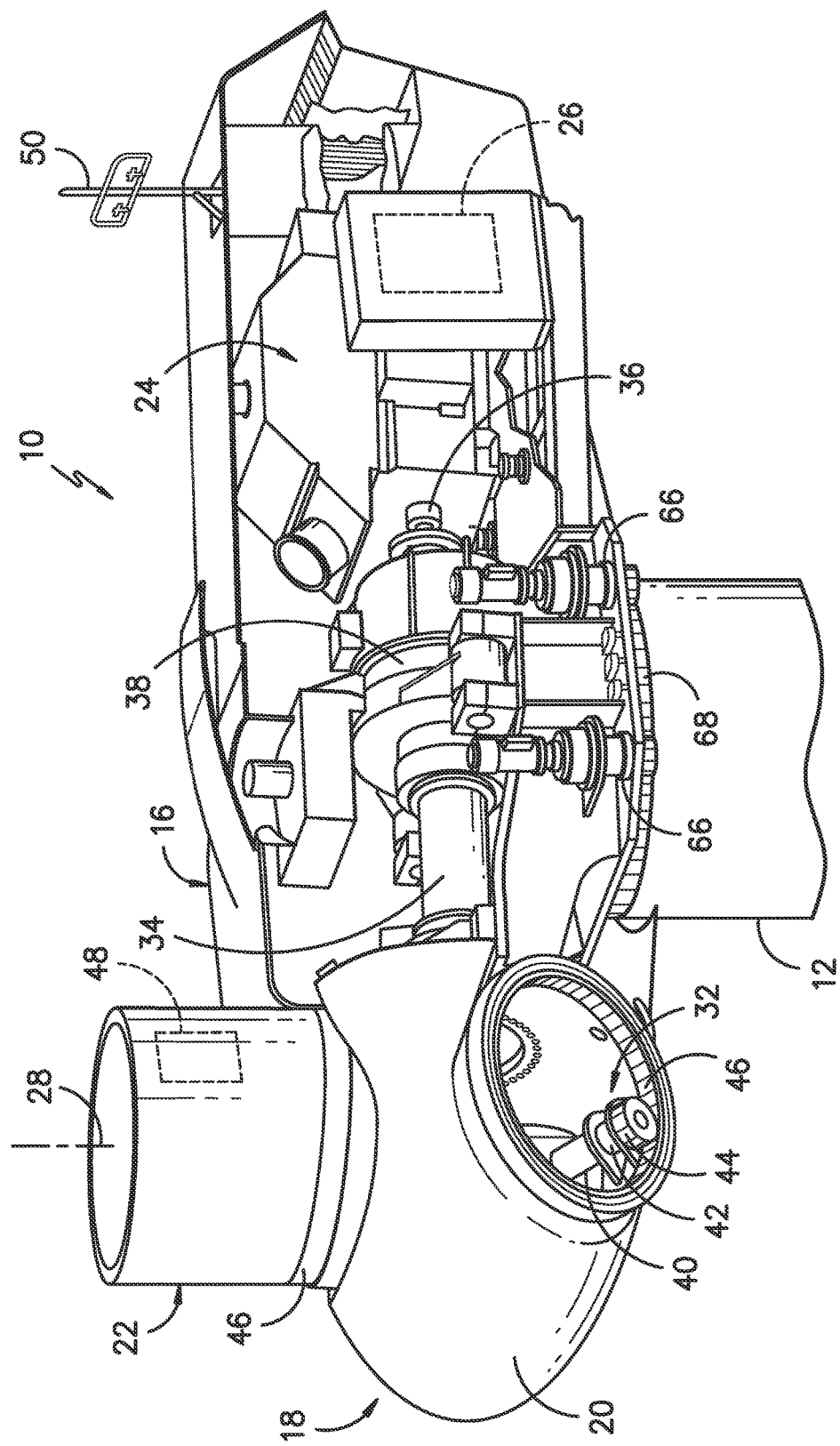
FIG. -2-

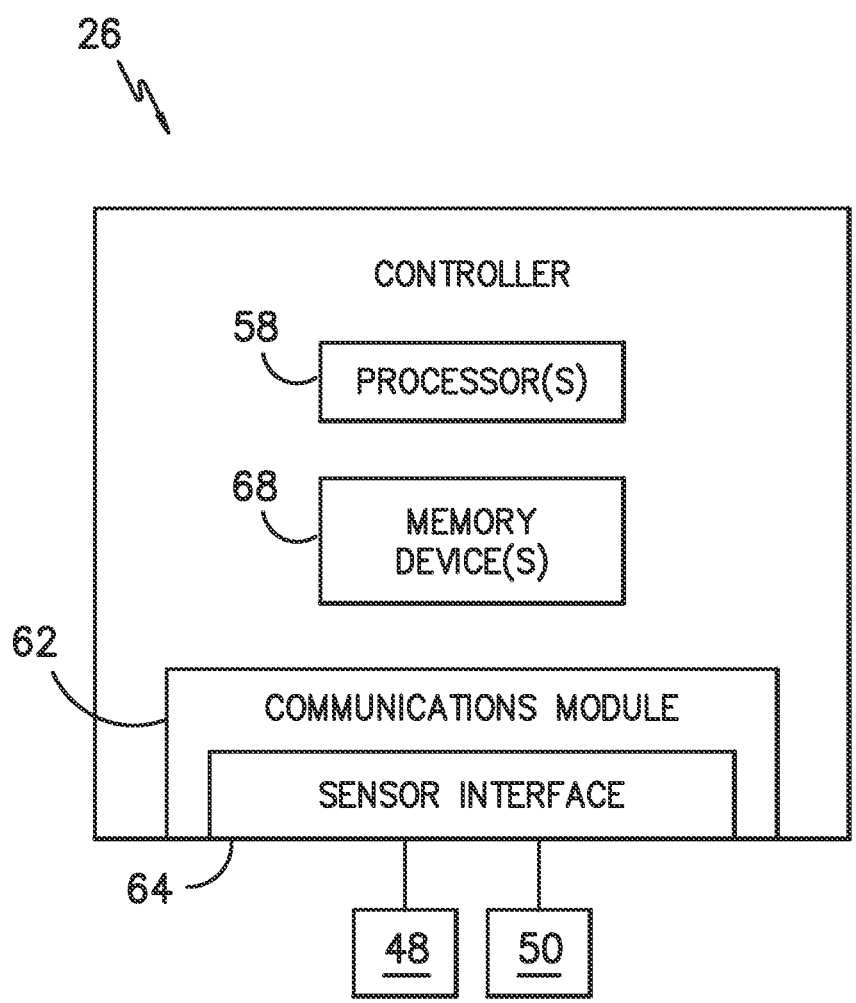
FIG. -3-

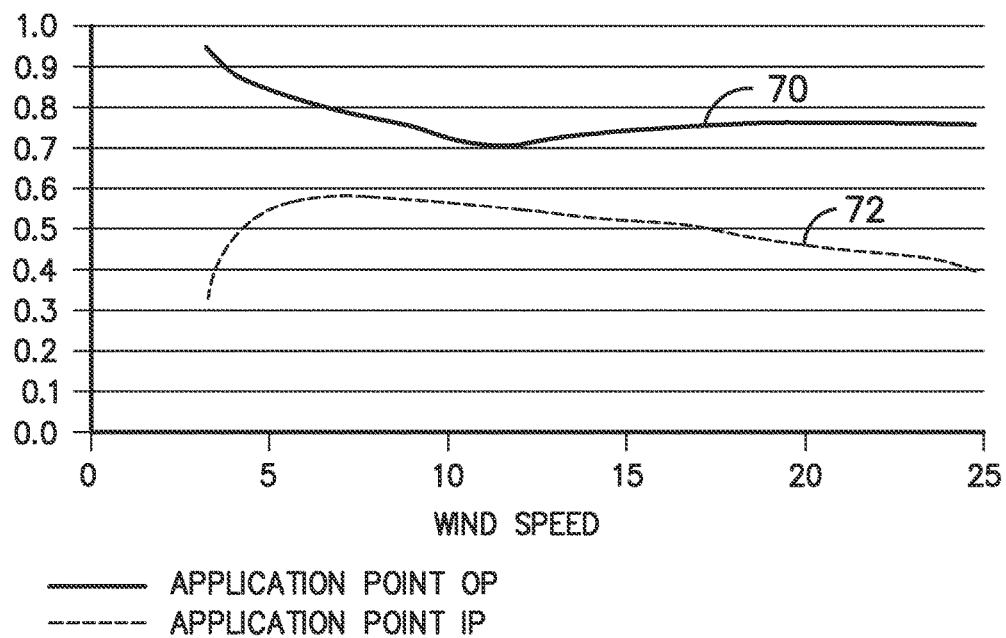
FIG. -4-
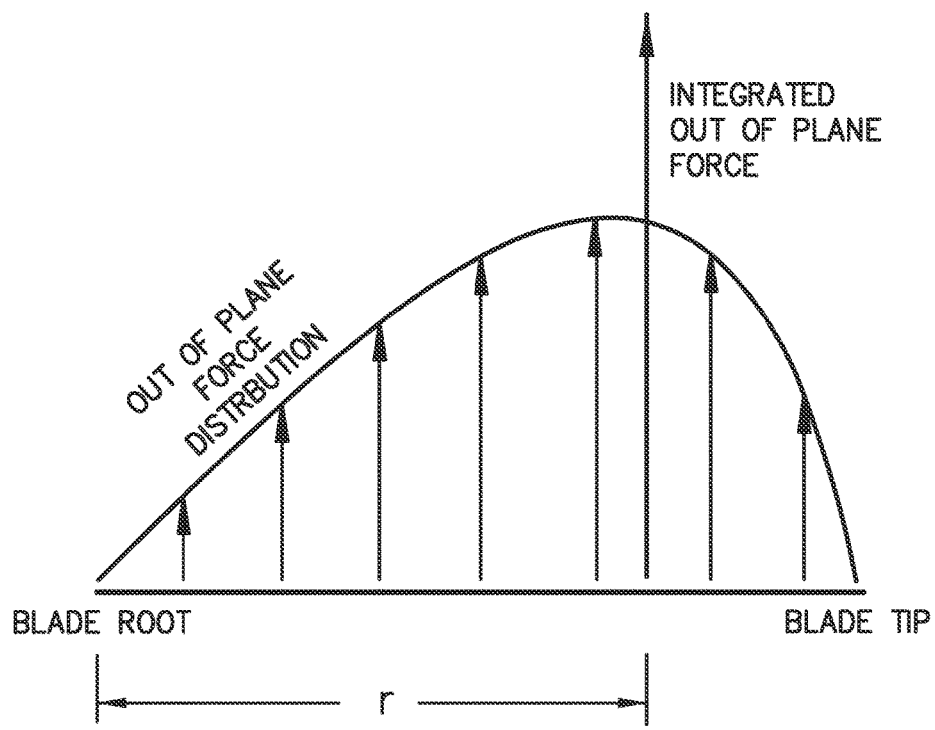
FIG. -5-

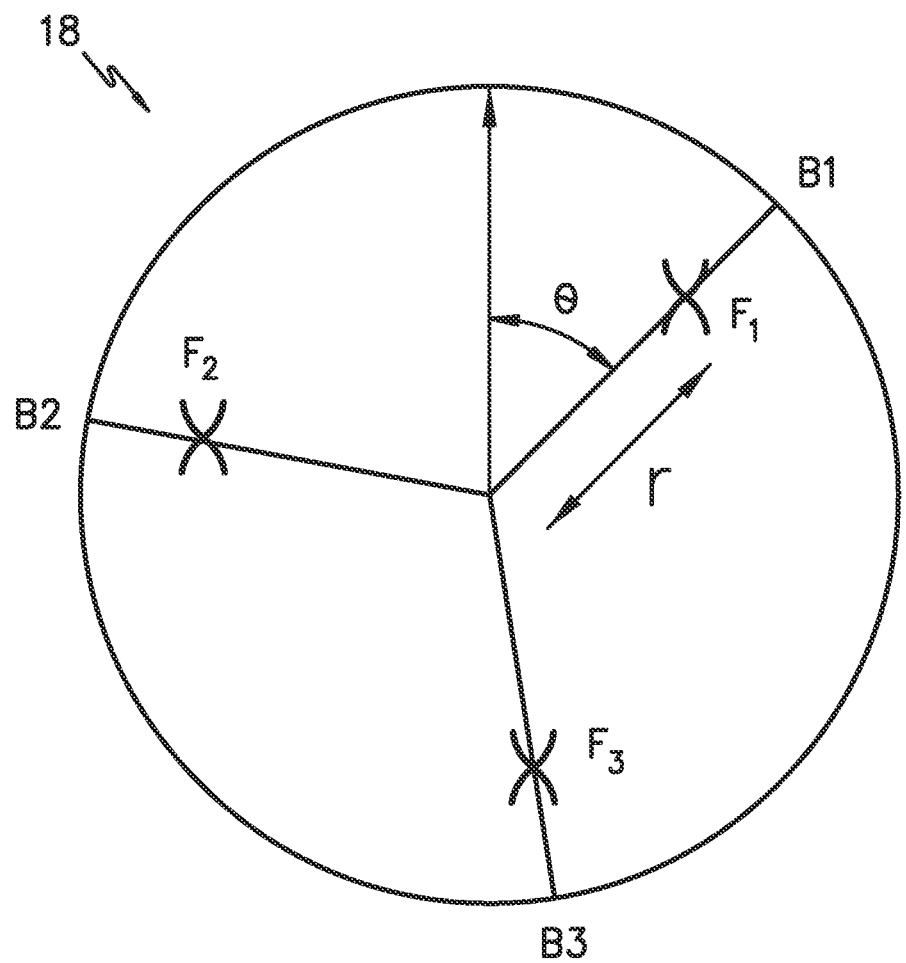
FIG. -6-

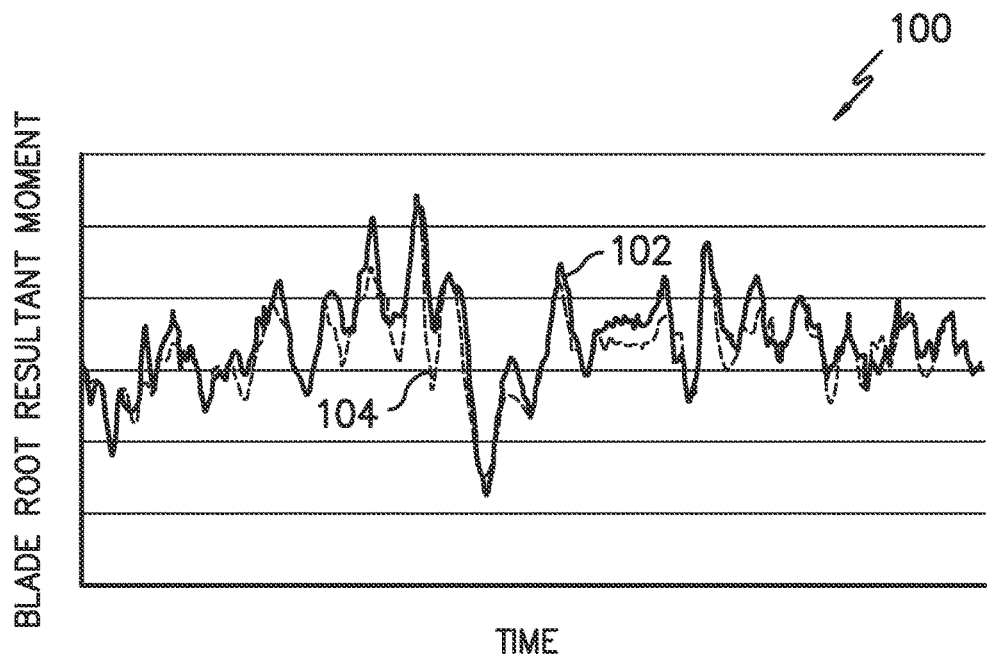
FIG. -7-
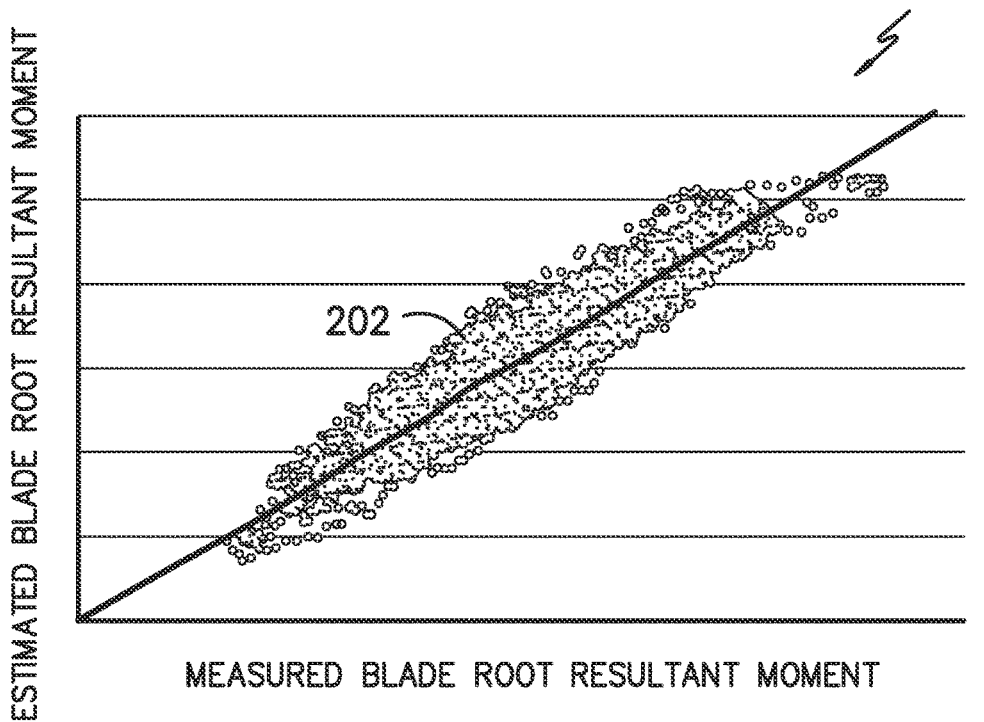
FIG. -8-

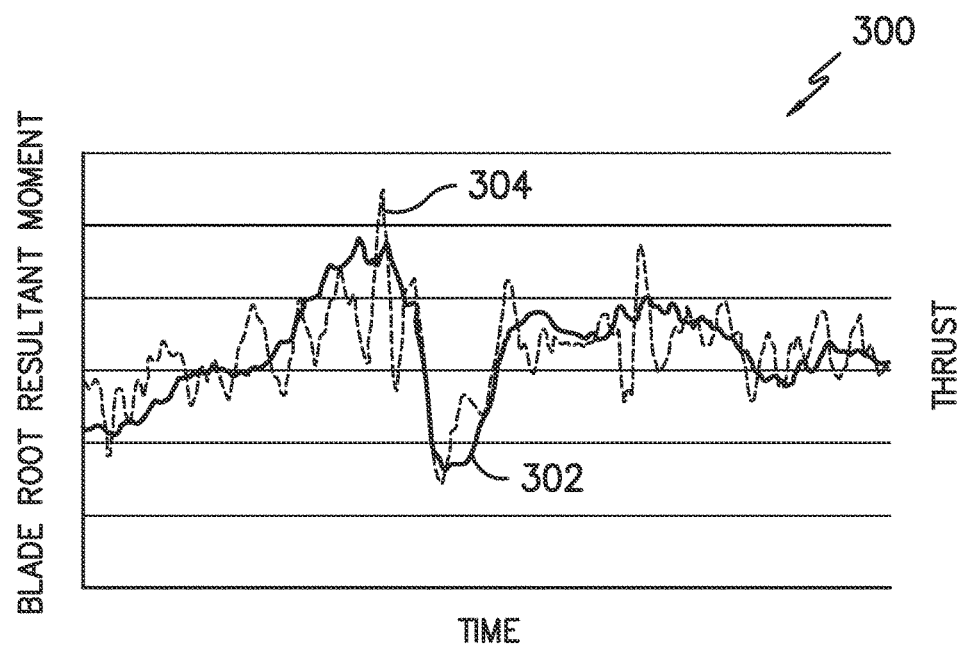
FIG. -9-
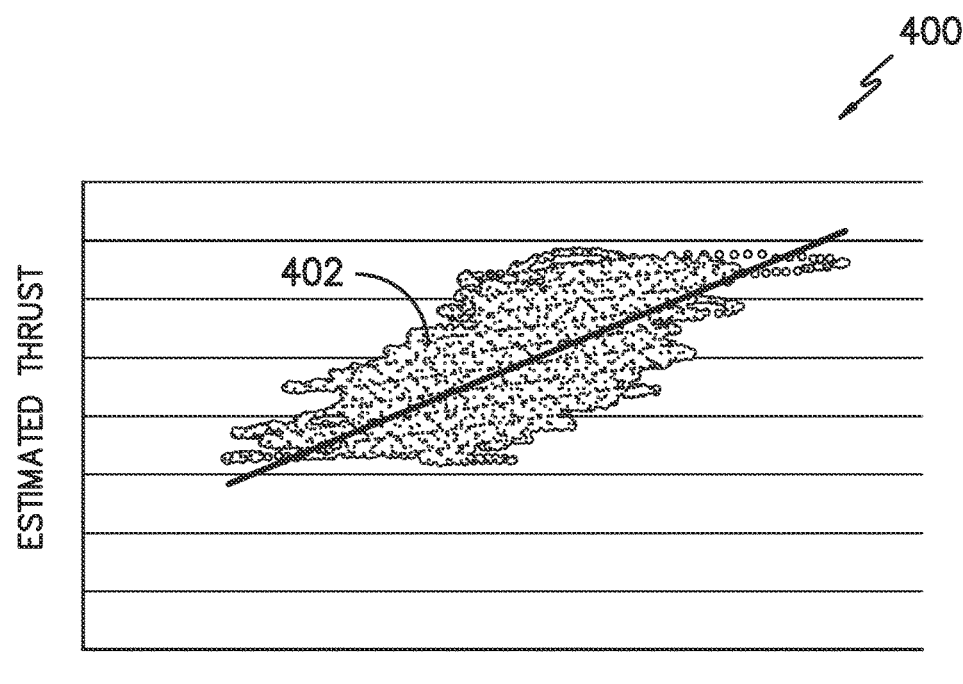
FIG. -10-

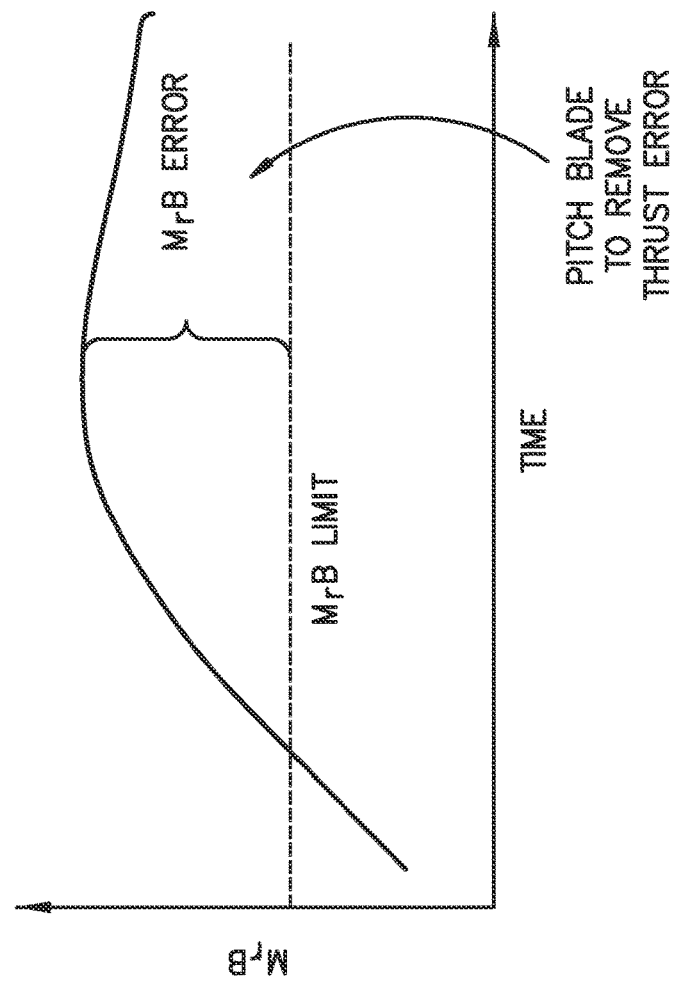
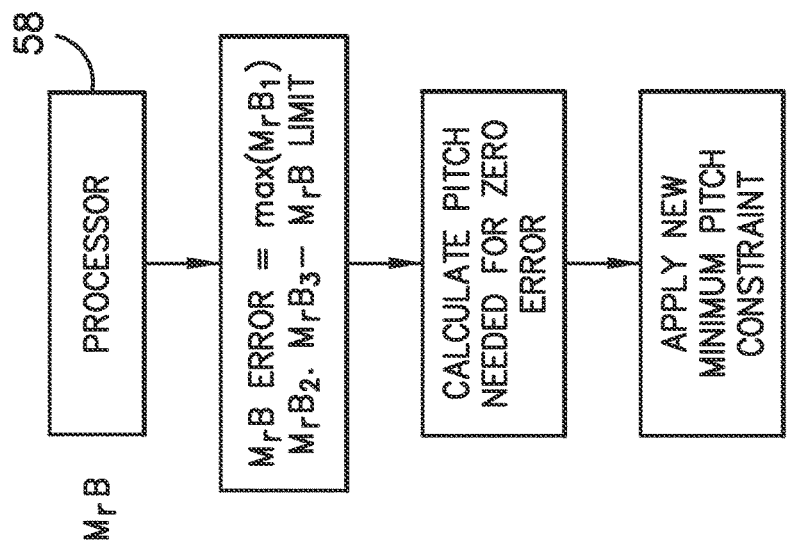
FIG. -11-

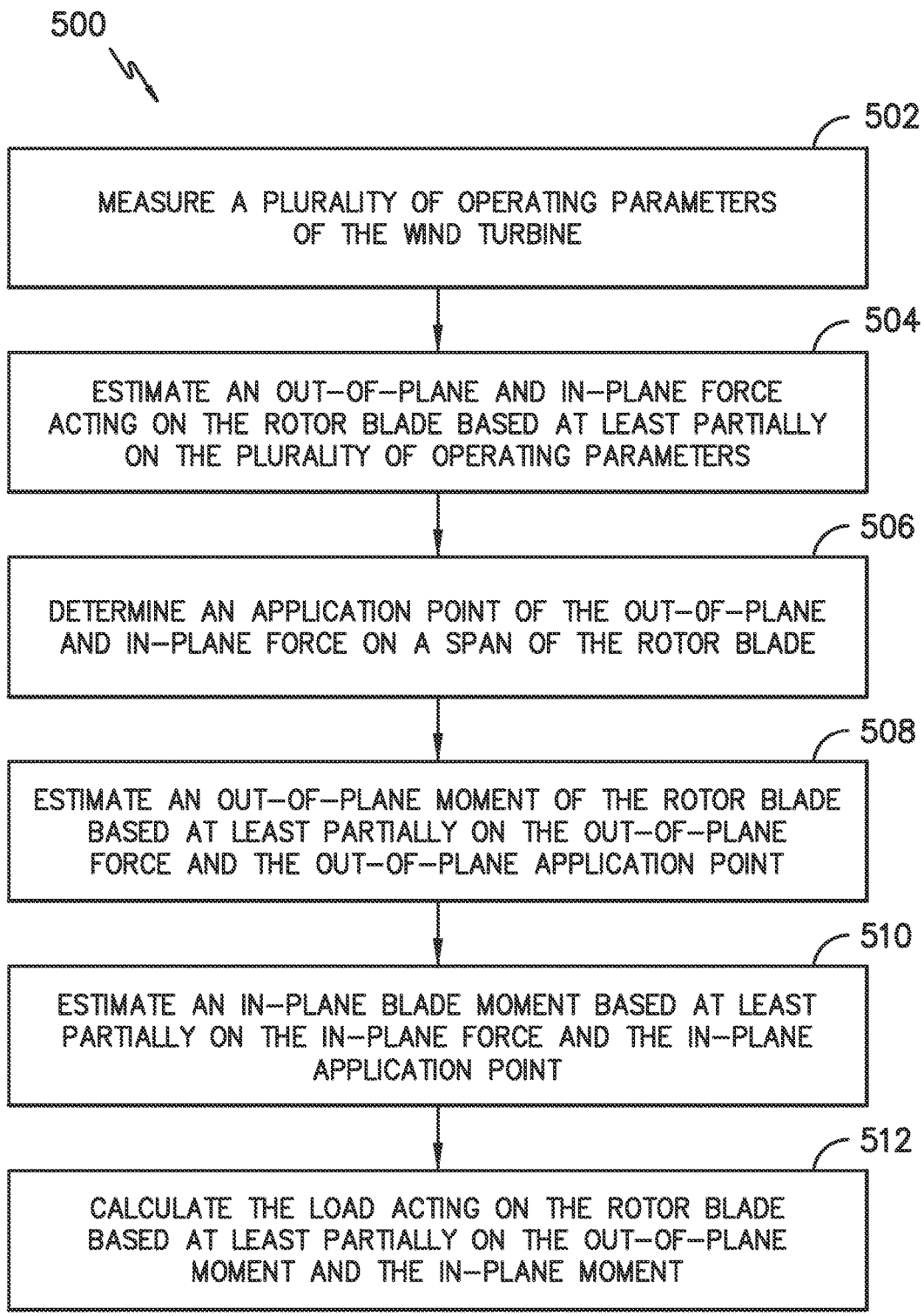
FIG. -12-

SYSTEM AND METHOD FOR ESTIMATING ROTOR BLADE LOADS OF A WIND TURBINE

FIELD OF THE INVENTION

The present subject matter relates generally to wind turbines and, more particularly, to a system and method for estimating rotor blade loads acting on a wind turbine.

BACKGROUND OF THE INVENTION

Wind power is considered one of the cleanest, most environmentally friendly energy sources presently available and wind turbines have gained increased attention in this regard. A modern wind turbine typically includes a tower, a generator, a gearbox, a nacelle, and one or more rotor blades. The rotor blades are the primary elements for converting wind energy into electrical energy. The blades typically have the cross-sectional profile of an airfoil such that, during operation, air flows over the blade producing a pressure difference between its sides. Consequently, a lift force, which is directed from the pressure side towards the suction side, acts on the blade. The lift force generates torque on the main rotor shaft, which is connected to a generator for producing electricity.

The amount of power that may be produced by a wind turbine is typically limited by structural limitations (i.e. design loads) of the individual wind turbine components. For example, the blade root of a wind turbine may experience loads (e.g. a blade root resultant moment) associated with both average loading due to turbine operation and dynamically fluctuating loads due to environmental conditions. Such loading may damage turbine components, thereby eventually causing the turbine components to fail. The fluctuating loads can change day-to-day or season-to-season and may be based on wind speed, wind peaks, wind turbulence, wind shear, changes in wind direction, density in the air, yaw misalignment, upflow, or similar. Specifically, for example, loads experienced by a wind turbine may vary with wind speed.

As such, it is imperative to ensure loads acting on the wind turbine do not exceed design loads. Thus, many wind turbines employ one or more sensors configured to measure the loads acting on the various wind turbine components. Though the sensors may provide the desired information, new sensor systems can be complex and expensive to install. Further, the sensors may provide inaccurate information and can be prone to fail.

Additionally, wind turbines utilize control systems configured to estimate loads acting on the wind turbine based on a wind turbine thrust. The terms "thrust," "thrust value," "thrust parameter" or similar as used herein are meant to encompass a force acting on the wind turbine due to the wind. The thrust force comes from a change in pressure as the wind passes the wind turbine and slows down. Such control strategies estimate loads acting on the wind turbine by determining an estimated thrust using a plurality of turbine operating conditions, such as, for example, pitch angle, power output, generator speed, and air density. The operating conditions are inputs for the algorithm, which includes a series of equations, one or more aerodynamic performance maps, and one or more look-up tables (LUTs). For example, the LUT may be representative of a wind turbine thrust. A +/−standard deviation of the estimated thrust may also be calculated, along with an operational maximum thrust and a thrust limit. As such, the wind turbine may be controlled based on a difference between the maximum thrust and the thrust limit.

In view of the foregoing, the art is continuously seeking new and improved systems for estimating loads acting on a wind turbine. Thus, a system and method for estimating rotor blade loads of a wind turbine, e.g. a blade root resultant moment of a rotor blade, would be desired in the art. Further, a system and method that incorporated existing hardware and software would be advantageous.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a method for estimating a rotor blade load, e.g. a blade root resultant moment, acting on a wind turbine. The method includes measuring, via one or more sensors, a plurality of operating parameters of the wind turbine. Another step includes estimating, via a processor, an out-of-plane and an in-plane force acting on the rotor blade based at least partially on the plurality of operating parameters. Further, the method includes determining, via the processor, an application point of the out-of-plane and in-plane forces on a span of the rotor blade. A further step includes estimating, via the processor, out-of-plane and in-plane moments of the rotor blade based at least partially on the out-of-plane and in-plane forces and the out-of-plane and in-plane application points. Thus, the method includes calculating, via the processor, the rotor blade load acting on the rotor blade based at least partially on the out-of-plane moment and the in-plane moment.

In one embodiment, the plurality of operating parameters of the wind turbine may include at least one of the following: a thrust, a power, a speed, a torque, a pitch angle, a nodding moment, an overhang moment, a rotor azimuth angle, a yawing moment, or any other operating parameter of the wind turbine. In another embodiment, the method may include estimating the thrust by utilizing at least one of the following: a plurality of equations, one or more aerodynamic performance maps, or one or more look-up tables.

In additional embodiments, the step of estimating the out-of-plane root force may include determining an out-of-plane force distribution from a blade root to a blade tip of the rotor blade and integrating the out-of-plane force distribution to obtain an equivalent out-of-plane force.

In still another embodiment, the step of determining the application point of the out-of-plane force may include determining a plurality of application points of a plurality of out-of-plane forces during operation of the wind turbine for a plurality of wind speeds and storing the plurality of application points in an aerodynamic performance map. In an alternative embodiment, the application point of the out-of-plane force may be a constant value.

In yet another embodiment, the method may include estimating the in-plane moment of the rotor blade as a function of at least one of a weight of the rotor blade, a mechanical torque load of the rotor blade, a speed of the rotor blade, a power of the rotor blade, or an inertial load of the rotor blade. More specifically, in one embodiment, the method may include calculating the gravity load of the rotor blade as a function of at least one of the rotor azimuth angle, a mass of the rotor blade, gravity, a hub radius, or a center of gravity location of the rotor blade. Further, the method may include calculating the mechanical torque load of the rotor blade as a function of at least one of a low-speed shaft torque or power, a blade radius, or the hub radius. In addition, the method may include calculating the inertial load of the rotor blade as a function of at least one of rotor acceleration or rotor inertia. In still further embodiments, the method may include determining the rotor acceleration based at least partially on a rate of change of a rotor speed signal and filtering the speed signal. More specifically, in one embodiment, the method may include filtering the speed signal via a low pass filter.

In additional embodiments, the method may also include estimating an in-plane shear force of the rotor blade as a function of at least one of the rotor azimuth angle, a rotor blade mass, a rotor blade radius, the application point, torque, filtered rotor acceleration, rotor inertia, gravity, aerodynamic drag, wind speed, and/or a center of gravity location. Further, the method may include calculating the load acting on the rotor blade based at least partially on the in-plane shear force.

In another aspect, the present disclosure is directed to a system for maintaining rotor blade loads of a wind turbine within predetermined limits while also maximizing power output. The system includes one or more sensors configured to measure a plurality of operating parameters of the wind turbine and a controller configured with the one or more sensors. In addition, the controller includes one or more processors configured to perform one or more operations. For example, in one embodiment, the operations may include estimating an out-of-plane force and an in-plane force acting on the rotor blade based at least partially on the plurality of operating parameters, determining an application point of the out-of-plane and in-plane forces on a span of the rotor blade, estimating an out-of-plane and an in-plane moment of the rotor blade based at least partially on the out-of-plane and in-plane forces and the out-of-plane and in-plane application points, and calculating the rotor blade load acting on the rotor blade based at least partially on the out-of-plane moment and the in-plane moment. It should be understood that the system may be further configured with any of the additional features as described herein and may implement any of the additional method steps as described herein as well.

In yet another aspect, the present disclosure is directed to a method for estimating an out-of-plane blade root moment of the rotor blade. The method includes measuring a plurality of operating parameters of the wind turbine. For example, the operating parameters may include at least one of the following: a thrust, a nodding moment, an overhang moment, a rotor azimuth angle, or a yawing moment. Another step includes estimating an out-of-plane force acting on the rotor blade based at least partially on the plurality of operating parameters. The method also includes determining an application point on the rotor blade of the out-of-plane force. Thus, the out-of-plane blade root moment is determined as a function of the out-of-plane force and the application point of the out-of-plane force.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of a wind turbine according to the present disclosure;

FIG. 2 illustrates a simplified, internal view of one embodiment of a nacelle of a wind turbine according to the present disclosure;

FIG. 3 illustrates a schematic diagram of one embodiment of a controller according to the present disclosure;

FIG. 4 illustrates a graph one embodiment of the application points for the out-of-plane and in-plane forces acting on a rotor blade as a function of wind speed according to the present disclosure;

FIG. 5 illustrates a schematic diagram of one embodiment of an out-of-plane force distribution of a rotor blade according to the present disclosure;

FIG. 6 illustrates a free body diagram (FBD) of one embodiment of a rotor of a wind turbine according to the present disclosure;

FIG. 7 illustrates a graph comparing the estimated blade root resultant moment and the measured blade root resultant moment according to one embodiment of the present disclosure;

FIG. 8 illustrates a graph of the measured blade root resultant moment plotted on the x-axis and the estimated blade root resultant moment plotted on the y-axis according to one embodiment of the present disclosure;

FIG. 9 illustrates a graph comparing the estimated thrust and the measured blade root resultant moment according to conventional construction;

FIG. 10 illustrates a graph of the measured blade root resultant moment plotted on the x-axis and the estimated thrust plotted on the y-axis according to conventional construction;

FIG. 11 illustrates a simplified flow diagram of one embodiment of steps taken by the controller to calculated a blade root resultant moment error according to the present disclosure; and FIG. 12 illustrates a flow diagram of one embodiment of a method for estimating a rotor blade load of a wind turbine according to the present disclosure.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present subject matter is directed to improved systems and methods for estimating rotor blade loads of a wind turbine. In one embodiment, for example, the system collects and stores operating parameters of the wind turbine. Thus, the system is configured to estimate an out-of-plane and an in-plane force acting on the rotor blade based on the operating parameters. The system is also configured to determine an application point of the out-of-plane and in-plane forces along a span of the rotor blade. As such, the system can then estimate an out-of-plane and in-plane blade root moment based on the out-of-plane and in-plane forces and the out-of-plane and in-plane application points. Accordingly, the system is configured to determine a blade root resultant moment of the rotor blade based at least partially on the out-of-plane blade root moment and the in-plane blade root moment.

The various embodiments of the system and method described herein provide numerous advantages. For example, the present disclosure maintains rotor blade loads within predetermined limits, while also maximizing annual energy production (AEP). Thus, the present disclosure can help prevent turbine component failure caused by excessive blade loading. Moreover, the present disclosure may be implemented using existing components of the wind turbine and does not require additional sensors. As such, a user is not required to purchase, install, and maintain new equipment. Moreover, the system may be integrated with a broader control system, such as, but not limiting of, a wind turbine control system, a plant control system, a remote monitoring system, or combinations thereof.

Referring now to FIG. 1, a perspective view of one embodiment of a wind turbine 10 that may implement the control technology according to the present disclosure is illustrated. As shown, the wind turbine 10 generally includes a tower 12 extending from a support surface 14, a nacelle 16 mounted on the tower 12, and a rotor 18 coupled to the nacelle 16. The rotor 18 includes a rotatable hub 20 and at least one rotor blade 22 coupled to and extending outwardly from the hub 20. For example, in the illustrated embodiment, the rotor 18 includes three rotor blades 22. However, in an alternative embodiment, the rotor 18 may include more or less than three rotor blades 22. Each rotor blade 22 may be spaced about the hub 20 to facilitate rotating the rotor 18 to enable kinetic energy to be transferred from the wind into usable mechanical energy, and subsequently, electrical energy. For instance, the hub 20 may be rotatably coupled to an electric generator 24 (FIG. 2) positioned within the nacelle 16 to permit electrical energy to be produced.

The wind turbine 10 may also include a wind turbine controller 26 centralized within the nacelle 16. However, in other embodiments, the controller 26 may be located within any other component of the wind turbine 10 or at a location outside the wind turbine. Further, the controller 26 may be communicatively coupled to any number of the components of the wind turbine 10 in order to control the operation of such components and/or to implement a correction action. As such, the controller 26 may include a computer or other suitable processing unit. Thus, in several embodiments, the controller 26 may include suitable computer-readable instructions that, when implemented, configure the controller 26 to perform various different functions, such as receiving, transmitting and/or executing wind turbine control signals. Accordingly, the controller 26 may generally be configured to control the various operating modes (e.g., start-up or shut-down sequences), de-rate the wind turbine, and/or control various components of the wind turbine 10 as will be discussed in more detail below.

Referring now to FIG. 2, a simplified, internal view of one embodiment of the nacelle 16 of the wind turbine 10 shown in FIG. 1 is illustrated. As shown, the generator 24 may be coupled to the rotor 18 for producing electrical power from the rotational energy generated by the rotor 18. For example, as shown in the illustrated embodiment, the rotor 18 may include a rotor shaft 34 coupled to the hub 20 for rotation therewith. The rotor shaft 34 may, in turn, be rotatably coupled to a generator shaft 36 of the generator 24 through a gearbox 38. As is generally understood, the rotor shaft 34 may provide a low speed, high torque input to the gearbox 38 in response to rotation of the rotor blades 22 and the hub 20. The gearbox 38 may then be configured to convert the low speed, high torque input to a high speed, low torque output to drive the generator shaft 36 and, thus, the generator 24.

Each rotor blade 22 may also include a pitch adjustment mechanism 32 configured to rotate each rotor blade 22 about its pitch axis 28. Further, each pitch adjustment mechanism 32 may include a pitch drive motor 40 (e.g., any suitable electric, hydraulic, or pneumatic motor), a pitch drive gearbox 42, and a pitch drive pinion 44. In such embodiments, the pitch drive motor 40 may be coupled to the pitch drive gearbox 42 so that the pitch drive motor 40 imparts mechanical force to the pitch drive gearbox 42. Similarly, the pitch drive gearbox 42 may be coupled to the pitch drive pinion 44 for rotation therewith. The pitch drive pinion 44 may, in turn, be in rotational engagement with a pitch bearing 46 coupled between the hub 20 and a corresponding rotor blade 22 such that rotation of the pitch drive pinion 44 causes rotation of the pitch bearing 46. Thus, in such embodiments, rotation of the pitch drive motor 40 drives the pitch drive gearbox 42 and the pitch drive pinion 44, thereby rotating the pitch bearing 46 and the rotor blade 22 about the pitch axis 28. Similarly, the wind turbine 10 may include one or more yaw drive mechanisms 66 communicatively coupled to the controller 26, with each yaw drive mechanism(s) 66 being configured to change the angle of the nacelle 16 relative to the wind (e.g., by engaging a yaw bearing 68 of the wind turbine 10).

Still referring to FIG. 2, the wind turbine 10 may also include one or more sensors 48, 50 for measuring various operating parameters that may be required to calculate the out-of-plane and in-plane moments as described in more detail below. For example, in various embodiments, the sensors may include blade sensors 48 for measuring a pitch angle of one of the rotor blades 22 or for measuring a load acting on one of the rotor blades 22; generator sensors (not shown) for monitoring the generator 24 (e.g. torque, rotational speed, acceleration and/or the power output); sensors for measuring the imbalance loading in the rotor (e.g. main shaft bending sensors); and/or various wind sensors 50 for measuring various wind parameters, such as wind speed, wind peaks, wind turbulence, wind shear, changes in wind direction, air density, or similar. Further, the sensors may be located near the ground of the wind turbine, on the nacelle, or on a meteorological mast of the wind turbine. It should also be understood that any other number or type of sensors may be employed and at any location. For example, the sensors may be Micro Inertial Measurement Units (MI-MUs), strain gauges, accelerometers, pressure sensors, angle of attack sensors, vibration sensors, proximity sensors, Light Detecting and Ranging (LIDAR) sensors, camera systems, fiber optic systems, anemometers, wind vanes, Sonic Detection and Ranging (SODAR) sensors, infra lasers, radiometers, pitot tubes, rawinsondes, other optical sensors, and/or any other suitable sensors. It should be appreciated that, as used herein, the term "monitor" and variations thereof indicates that the various sensors may be configured to provide a direct measurement of the parameters being monitored or an indirect measurement of such parameters. Thus, the sensors may, for example, be used to generate signals relating to the parameter being monitored, which can then be utilized by the controller 26 to determine the actual parameter.

Referring now to FIG. 3, there is illustrated a block diagram of one embodiment of various components of the controller 26 according to the present disclosure. As shown, the controller 26 may include one or more processor(s) 58 and associated memory device(s) 60 configured to perform a variety of computer-implemented functions (e.g., performing the methods, steps, calculations and the like and storing relevant data as disclosed herein). Additionally, the controller 26 may also include a communications module 62 to facilitate communications between the controller 26 and the various components of the wind turbine 10. Further, the communications module 62 may include a sensor interface 64 (e.g., one or more analog-to-digital converters) to permit signals transmitted from the sensors 48, 50 to be converted into signals that can be understood and processed by the processors 58. It should be appreciated that the sensors 48, 50 may be communicatively coupled to the communications module 62 using any suitable means. For example, as shown in FIG. 3, the sensors 48, 50 are coupled to the sensor interface 64 via a wired connection. However, in other embodiments, the sensors 48, 50 may be coupled to the sensor interface 64 via a wireless connection, such as by using any suitable wireless communications protocol known in the art.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 60 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 60 may generally be configured to store suitable computer-readable instructions that, when implemented by the processor(s) 58, configure the controller 26 to perform various functions including, but not limited to, determining one or more current wind turbine parameters of the wind turbine 10 based on the plurality of operating data, determining a maximum wind turbine parameter, transmitting suitable control signals to implement control actions to reduce loads acting on the wind turbine, and various other suitable computer-implemented functions.

The processor 58 is configured to utilize the measured operating parameters from the sensors 48, 50 to estimate rotor blade loads (e.g. blade root resultant moments and/or forces) of the wind turbine 10. For example, the sensors 48, 50 are configured to measure various wind turbine and/or environmental conditions, so as to directly or indirectly provide information regarding one or more of the following parameters: a rotor thrust, a mechanical torque, in-plane and out-of-plane application points of forces acting on the rotor blades 22, rotor imbalance measurements, a rotor azimuth angle, rotor speed, a gearbox ratio, a nodding moment, an overhang moment, a yawing moment, gravity, a hub radius, a blade radius, a cone angle, a blade mass, a blade weight, a center of gravity location for each of the rotor blades 22, or any other operating parameter of the wind turbine 10. More specifically, Table 1 below illustrates one sample set of inputs that may be used by the processor 58 to estimate the load estimations as described herein.

TABLE 1

Description of Blade Root Resultant Moment Estimation Inputs

| Parameter | Description |
|---|---|
| ApplicationPointOP | Fraction radius along blade where integrated aerodynamic thrust force is applied |
| ApplicationPointIP | Fraction radius along blade where integrated aerodynamic in-plane force is applied |
| RotorAccTC | 1st order low pass filter time constant for rotor acceleration signal |
| BladeRadius | Blade Radius |
| BladeMass | Blade Mass |
| Rotor Inertia | Spinning inertia |
| Cone Angle | Rotor cone angle |
| CGloc | Application point of center of gravity from rotor apex |
| HubCO | Hub Radius |
| Gearbox Ratio | Gearbox Ratio |
| Overhang Moment | Rotor + Hub overhang moment about hub flange location |
| Gravity | Gravity |

In most embodiments, the inputs of Table 1 are readily available and easy to calculate and/or measure; however, the present disclosure provides unique methods for calculating one or more of the parameters, e.g. ApplicationPointOP and ApplicationPointIP. More specifically, in one embodiment, the ApplicationPointOP is a function of tip speed ratio (TSR) and pitch angle and can be defined throughout the turbine operation as shown in Equation (1) below:

$$ApplicationPoint\ OP(TSR, \text{pitch angle}) = \frac{Nblades * OutofPlane\ \text{Moment}(TSR, \text{pitch angle})}{\text{Thrust}(TSR, \text{pitch angle}) * \text{Blade Radius}} \quad \text{Equation (1)}$$

where

Nblades is equal to the number of blades on the wind turbine.

Further, ApplicationPointIP can be defined in a similar fashion with Equation (2) below:

$$ApplicationPointIP(TSR, \text{pitch angle}) = \frac{\text{Torque}(TSR, \text{pitch angle})}{Nblades * \text{In-Plane Shear Force}(TSR, \text{pitch angle}) * \text{Blade Radius}} \quad \text{Equation (2)}$$

Thus, the calculated values for ApplicationPointOP and ApplicationPointIP may be stored in the memory device 60 in a table. Accordingly, in one embodiment, the values may be averaged and the average ApplicationPointOP and ApplicationPointIP can be used to calculate the blade root resultant moment which is described in more detail below.

Referring now to FIG. 4, a graph of ApplicationPointOP and ApplicationPointIP values as a function of wind speed for nominal turbine operation is illustrated. More specifically, as shown, the average ApplicationPointOP is approximately 0.75 (i.e. located at 75% span of the rotor blade 22), whereas the average ApplicationPointIP is approximately 0.5 (i.e. located at 50% span of the rotor blade 22), which are provided as mere examples of suitable ApplicationPointOP and ApplicationPointIP values.

In an alternative embodiment, ApplicationPointOP and ApplicationPointIP may be calculated during the aerodynamic performance map process. The aerodynamic performance maps as described herein are dimensional or non-dimensional tables that describe rotor loading and performance (e.g. power, thrust, torque, or bending moment, or similar) under given conditions (e.g. density, wind speed, rotor speed, pitch angles, or similar). As such, the aerodynamic performance maps may include: a power coefficient, a thrust coefficient, a torque coefficient, and/or partial derivatives with respect to pitch angle, rotor speed, and tip speed ratio (TSR), and in this case, the application points of the forces acting on the rotor blade. Alternatively, the aerodynamic performance maps can be dimensional power, thrust, and/or torque values instead of coefficients. Thus, in a certain embodiment, the processor 58 is configured to determine the out-of-plane application point by determining a plurality of application points of a plurality of out-of-plane forces during operation of the wind turbine for a plurality of wind speeds and storing the plurality of application points in an aerodynamic performance map. This approach allows for more accurate blade root loading estimations during off-nominal operating periods, as such application points of force vary as a function of wind speed/rotor speed (tip-speed ratio) and pitch angle (off-nominal operation is typically when peak loads occur). In further embodiments, the processor 58 is configured to prevent introduction of a structural stiffness or turbine geometry dependency into the aerodynamic performance maps when integrating ApplicationPointOP and ApplicationPointIP. For example, as shown in FIG. 5, a schematic diagram of one embodiment of an out-of-plane force distribution from the blade root to the blade tip of the rotor blade 22 is illustrated. By integrating the area under the out-of-plane force distribution curve, the integrated or equivalent out-of-place force and corresponding application point r along the rotor blade 22 can be determined.

Accordingly, the processor 58 is configured to utilize the operating parameters, as well as ApplicationPointOP and ApplicationPointIP, to estimate various load components of the blade root resultant moment, including at least, an out-of-plane shear force, an in-plane shear force, an axial force, an out-of-plane blade root moment, an in-plane blade root moment, and a blade torsion. It should be understood that the blade root resultant moment calculations as described herein are directed to the wind turbine 10 having three rotor blades 22; however, such calculations are provided for example purposes only and are not meant to be limiting. Thus, the calculations as described herein may be applied to a wind turbine having any suitable number of blades. In addition, in various embodiments, it is assumed that the ApplicationPointOP and ApplicationPointIP is the same for all three rotor blades and does not vary with individual blade TSR and/or pitch angle.

More specifically, in certain embodiments, the processor 58 is configured to calculate the out-of-plane root moment of each rotor blade 22 as a function of one or more of the out-of-plane application point r of the force (i.e. ApplicationPointOP), the blade radius, the center of gravity location, gravity, rotor imbalance load, and/or the rotor azimuth angle. For example, referring now to FIG. 6, a free body diagram (FBD) of the wind turbine rotor 18 is illustrated. As shown, the rotor azimuth angle θ is referenced from rotor blade 1 (i.e. B1), with θ increasing as the blades (i.e. B1, B2, and B3) rotate in a clockwise manner. Thus, θ is between 0° and 360° with 0° being defined as B1 at the 12 o'clock position. The blade forces, namely forces $F_1$, $F_2$, $F_3$, are the out-of-plane forces going "into the page" due to aerodynamics (but neglecting centrifugal load from spinning mass with a coned rotor). Such forces are assumed to be applied at respective application points r, which are assumed to be the same for all three rotor blades.

Thus, the three equations shown below (Equations 3-5) having three unknowns (i.e. forces $F_1$, $F_2$, $F_3$) can be developed and solved using various methods known in the art.

$$\text{Estimated Thrust} = F_1 + F_2 + F_3 \quad\quad \text{Equation (3)}$$

$$\text{Measured Nodding Moment} - \text{Static Overhang Moment} = F_1 r \cos(\theta) + F_2 r \cos(\theta - 120°) + F_3 r \cos(\theta - 240°) \quad\quad \text{Equation (4)}$$

$$\text{Measured Yawing Moment} = F_1 r \sin(\theta) + F_2 r \sin(\theta - 120°) + F_3 r \sin(\theta - 240°) \quad\quad \text{Equation (5)}$$

The estimated thrust can be determined using a variety of techniques. For example, in one embodiment, the wind parameter estimator 56 may be configured to implement a control algorithm having a series of equations to determine the estimated thrust. As such, the equations are solved using one or more operating parameters, one or more aerodynamic performance maps, one or more LUTs, or any combination thereof. As mentioned, the aerodynamic performance maps describe rotor loading and performance (e.g. power, thrust, torque, or bending moment, or similar) under given conditions (e.g. density, wind speed, rotor speed, pitch angles, or similar). In addition, the LUTs may include: blade loads, tower loads, shaft loads, or any other wind turbine component load.

The measured nodding moment can also be determined using a variety of techniques. Further, it should be understood that the measured nodding moment as referred to herein generally refers to the aerodynamically induced nodding moment of the rotor 18. For example, in one embodiment, the measured nodding moment is equal to the nodding moment which provides 0 kNm when the wind speed is 0 meters/second.

In the illustrated embodiment, the Overhang Moment of Equation (4) and the Measured Yawing Moment of Equation (5) can be determined from the one or more sensors 48, 50. More specifically, in a particular embodiment, the sensors 48, 50 may be proximity probe measurement devices.

Once the processor 58 solves Equations 3-5 for the three unknowns, namely forces $F_1$, $F_2$, $F_3$, the processor 58 is configured to determine the out-of-plane bending moment for each of the rotor blades 22. More specifically, in one embodiment, the processor 58 calculates the out-of-plane blade root bending moment using Equation (6) below:

$$\text{Outofplane Bending Moment} = F \ast \text{ApplicationPointOP} \ast \text{Blade Radius} - \text{HubCO} \quad\quad \text{Equation (6)}$$

where
F is equal to the corresponding force acting on the rotor blade, e.g. $F_1$, $F_2$, or $F_3$.

As mentioned, the processor 58 is also configured to estimate an in-plane blade root moment of the rotor blade 22. More specifically, in a particular embodiment, the processor 58 is configured to estimate the in-plane blade root moment of the rotor blade 22 as a function of at least one of a weight of the rotor blade 22, a mechanical torque load of the rotor blade, and/or an inertial load of the rotor blade 22. For example, the processor 58 may calculate the weight of the rotor blade 22 as a function of at least one of the rotor azimuth angle, a rotor blade mass, gravity, a hub radius, or a center of gravity location of the rotor blade, as shown in Equation (7) below:

$$\text{Blade Weight Load} = -\sin(\theta) * \text{BladeMass} * \text{Gravity} * (CG_{loc} - \text{Hub}_{CO}) \quad \text{Equation (7)}$$

In a further embodiment, the processor 58 is configured to calculate the mechanical torque load of the rotor blade 22 as a function of at least one of a low-speed shaft torque, a blade radius, or the hub radius, as shown in Equation (8) below:

$$\text{Mechanical Torque Load} = \frac{\text{Torque}}{\text{Nblades}} * \frac{(\text{BladeRadius} - \text{Hub}_{CO})}{\text{BladeRadius}} \quad \text{Equation (8)}$$

In still another embodiment, the processor 58 is configured to calculate the inertial load of the rotor blade 22 as a function of at least one of a rotor acceleration or a rotor inertia, as shown in Equation (9) below:

$$\text{Inertial Load} = \text{RotorAcceleration}_{filtered} * \frac{\text{RotorInertia}}{\text{Nblades}} \quad \text{Equation (9)}$$

In various embodiments, each rotor blade 22 contributes equally to the rotor acceleration. Thus, in certain embodiments, the aerodynamic in-plane loads are equal on all rotor blades 22 and only change as fast as the mechanical torque. The in-plane inertial loading from rotor acceleration is important to the overall in-plane load. Thus, to capture this effect, the processor 58 may determine the rotor acceleration based at least partially on a rate of change of a rotor speed signal and filtering the speed signal. More specifically, in one embodiment, the processor 58 may filter the speed signal via a low pass filter. As such, the low-pass filter may pass low-frequency signals but attenuate (i.e. reduce the amplitude of) signals with frequencies higher than a cutoff frequency. The low-frequency signals may be then subtracted from the raw signal such that only the high-frequency signals remain. In further embodiments, the low-pass filter may be used in conjunction with a high-pass filter. Further, any number of low-pass filters or high-pass filters may be used in accordance with the present disclosure.

Alternatively the processor 58 may filter the speed signal via a high-pass filter. As such, the high pass filter may pass high-frequency signals but attenuate signals with frequencies lower than a cutoff frequency.

After calculating the blade weight load, the mechanical torque load, and the inertial load of the rotor blade 22, the in-plane blade root bending moment can be calculated using Equation (10) below:

$$\text{InPlane Bending Moment} = \text{Blade Weight Load} + \text{Mechanical Torque Load} + \text{Inertial Load} \quad \text{Equation (10)}$$

As mentioned, the processor 58 may also be configured to determine further blade loading components in addition to the out-of-plane blade root moment and the in-plane blade root moment, e.g. blade axial forces, out-of-plane shear forces, in-plane shear forces, and/or blade torsion. In certain embodiments, such load components may have lesser impact to the overall blade root load state and may be omitted.

More specifically, in one embodiment, the processor 58 is configured to calculate the blade axial force of each rotor blade 22 as a function of at least one of rotor blade mass, wind speed, center of gravity location, gravity, and/or the rotor azimuth angle. Thus, in further embodiments, the processor 58 may also calculate the out-of-plane shear force for each rotor blade 22 as a function of at least the rotor blade's axial load and the cone and tilt angles. In additional embodiments, the processor 58 is configured to calculate the in-plane shear force of each rotor blade 22 as a function of at least one of the rotor azimuth angle, rotor blade mass, blade radius, ApplicationPointIP, torque, filtered rotor acceleration, rotor inertia, gravity, aerodynamic drag, wind speed, and/or center of gravity location. For example, in one embodiment, the in-plane shear force for each rotor blade 22 can be calculated using Equation (11) below:

$$\text{InPlane Shear Force} = \sin(\theta) * \text{BladeMass} * \text{Gravity} + \frac{\text{Drag} * \text{Wind Speed}}{\text{ApplicationPointIP} * \text{BladeRadius}} - \frac{\frac{\text{Torque}}{\text{Nblades}}}{\text{ApplicationPointIP} * \text{BladeRadius}} + \frac{\frac{\text{RotorAccTc} * \text{RotorInertia}}{\text{Nblades}}}{\text{CGloc}} \quad \text{Equation (11)}$$

where
RotorAccTC is the first order low pass filter time constant for the rotor acceleration signal and can be set based on the quality of the speed measurement signal.

After calculating the individual blade load components, the processor 58 is configured to calculate the overall blade root resultant moment of the rotor blade 22 based at least partially on the out-of-plane blade root bending moment and the in-plane blade root bending moment. For example, in one embodiment, the overall blade root resultant moment can be calculated using Equation (12) below:

$$\text{Blade Root Resultant Moment} = \sqrt{\text{OutofPlane Bending Moment}^2 + \text{InPlane Bending Moment}^2} \quad \text{Equation (12)}$$

Referring now to FIGS. 7-10, various graphs illustrating the accuracy of the present disclosure as compared to measured data and/or previous load estimation methods are illustrated. More specifically, as shown in FIG. 7, a graph 100 of one embodiment of the estimated blade root resultant moment 102 as calculated by the present disclosure and the measured blade root resultant moment 104 as a function of time is illustrated. As shown, the accuracy of the present disclosure is illustrated by the close correlation between the estimated blade root resultant moment 102 and the measured blade root resultant moment 104. In addition, as shown in graph 200 of FIG. 8, the data from FIG. 7 is plotted differently with the measured blade root resultant moment on the x-axis and the estimated blade root resultant moment on the y-axis. As shown, the slope of the data 202 is approximately one to further illustrate the accuracy of the estimated blade root resultant moment of the present disclosure.

In contrast, as shown in the graph 300 of FIG. 9, the estimated thrust 302 as calculated according to previous methods known in the art is plotted against the measured blade root resultant moment 304. As shown, the estimated thrust 302 is less correlated to the measured blade root resultant moment 304 as the data provided in FIG. 7. In addition, as shown in graph 400 of FIG. 10, the data 402 is plotted with the measured blade root resultant moment on the x-axis and the estimated thrust on the y-axis. As shown, the data 402 is much less correlated than the graph of FIG. 8, having a slope of much less than one.

Due to the accuracy of the algorithm for estimating the blade root resultant moment of the present disclosure, the controller 26 of the present disclosure is capable of more accurately controlling loads of the wind turbine 10 without unduly sacrificing AEP. For example, as shown in FIG. 11, the processor 58 is configured to estimate the blade root resultant moment (e.g. MrB) and then determine the MrB Error using a variety of suitable methods. For example, in one embodiment, the wind turbine parameter estimator 56 is configured to calculate the MrB Error based on Equation (13) below:

$$\text{MrB Error} = \max(\text{MrB}_1, \text{MrB}_2, \text{MrB}_3) - \text{MrBLimit} \quad \text{Equation (13)}$$

where
$\text{MrB}_1$ is the blade root resultant moment from a first rotor blade,
$\text{MrB}_2$ is the blade root resultant moment from a second rotor blade,
$\text{MrB}_3$ is the blade root resultant moment from a third rotor blade, and
MrBLimit is the blade root resultant moment limit that prevents damage to the turbine components.

Based on the error, the controller 26 may determine and implement a control action needed for zero or near zero error. For example, the controller 26 may calculate a pitch angle for one or more of the rotor blades 22 and apply the new pitch constraint to reach zero error. Further, it should be understood that the control action as described herein may encompass any suitable command or constraint by the controller 26. For example, in several embodiments, the control action may include temporarily de-rating or up-rating the wind turbine to prevent excessive loads on one or more of the wind turbine components. Up-rating the wind turbine, such as by up-rating torque, may temporarily slow down the wind turbine and act as a brake to help reduce or prevent loading. De-rating the wind turbine may include speed de-rating, torque de-rating or a combination of both. Further, as mentioned, the wind turbine 10 may be de-rated by pitching one or more of the rotor blades 22 about its pitch axis 28. More specifically, the controller 26 may generally control each pitch adjustment mechanism 32 in order to alter the pitch angle of each rotor blade 22 between 0 degrees (i.e., a power position of the rotor blade 22) and 90 degrees (i.e., a feathered position of the rotor blade 22). As such, in one embodiment, the controller 26 may command a new pitch setpoint (e.g. from 0 degrees to 5 degrees), whereas in another embodiment, the controller 26 may specify a new pitch constraint (e.g. a constraint to ensure that subsequent pitch commands are at least 5 degrees).

In still another embodiment, the wind turbine 10 may be temporarily de-rated by modifying the torque demand on the generator 24. In general, the torque demand may be modified using any suitable method, process, structure and/or means known in the art. For instance, in one embodiment, the torque demand on the generator 24 may be controlled using the controller 26 by transmitting a suitable control signal/command to the generator 24 in order to modulate the magnetic flux produced within the generator 24.

The wind turbine 10 may also be temporarily de-rated by yawing the nacelle 22 to change the angle of the nacelle 16 relative to the direction of the wind. In further embodiments, the controller 26 may be configured to actuate one or more mechanical brake(s) in order to reduce the rotational speed of the rotor blades 22, thereby reducing component loading. In still further embodiments, the controller 26 may be configured to perform any appropriate control action known in the art. Further, the controller 26 may implement a combination of two or more control actions.

Referring now to FIG. 12, a flow diagram of method 500 according to one embodiment of the present disclosure is illustrated. As shown, the method 500 includes a first step 502 of measuring a plurality of operating parameters of the wind turbine. Another step 504 includes estimating an out-of-plane force acting on the rotor blade based at least partially on the plurality of operating parameters. The method 500 also includes a step 506 of determining an application point of the out-of-plane force along a span of the rotor blade. A further step 508 includes estimating an out-of-plane moment of the rotor blade based at least partially on the out-of-plane force and the application point. Another step 510 includes estimating an in-plane blade moment of the rotor blade. The method 500 may then include a step 512 of calculating the load acting on the rotor blade based at least partially on the out-of-plane moment and the in-plane moment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:
1. A method for reducing loads acting on a rotor blade of a wind turbine, the method comprising:
    measuring, via one or more sensors, a plurality of operating parameters of the wind turbine,
    estimating, via a turbine controller of the wind turbine, an out-of-plane force and an in-plane force acting on the rotor blade based at least partially on the plurality of operating parameters;
    calculating, via the turbine controller, an application point of the out-of-plane force and the in-plane force on a span of the rotor blade as a function of a tip-speed ratio and a pitch angle of the rotor blade;
    estimating, via the turbine controller, an out-of-plane moment of the rotor blade based at least partially on the out-of-plane force and the out-of-plane application point;

estimating, via the turbine controller, an in-plane blade moment of the rotor blade based at least partially on the in-plane force and the in-plane application point;

calculating, via the turbine controller, the load acting on the rotor blade based at least partially on the out-of-plane moment and the in-plane moment; and, implementing, via the turbine controller, a control action based on the calculated load, the control action comprising at least one of pitching the rotor blade, yawing a nacelle of the wind turbine, derating the wind turbine, uprating the wind turbine, or shutting down the wind turbine.

2. The method of claim 1, wherein the load acting on the rotor blade corresponds to a blade root resultant moment.

3. The method of claim 1, wherein the plurality of operating parameters of the wind turbine comprise at least one of the following: a thrust, a power, a speed, a torque, a pitch angle, a nodding moment, an overhang moment, a rotor azimuth angle, or a yawing moment.

4. The method of claim 3, further comprising estimating the thrust utilizing at least one of the following: a plurality of equations, one or more aerodynamic performance maps, or one or more look-up tables.

5. The method of claim 1, wherein estimating the out-of-plane force further comprises:
determining an out-of-plane force distribution from a blade root to a blade tip of the rotor blade; and
integrating the out-of-plane force distribution to obtain an equivalent out-of-plane force.

6. The method of claim 1, wherein determining the application point of the out-of-plane force further comprises:
determining a plurality of application points of a plurality of out-of-plane forces during operation of the wind turbine for a plurality of wind speeds; and
storing the plurality of application points in an aerodynamic performance map.

7. The method of claim 1, wherein the application point of the out-of-plane force comprises a constant value.

8. The method of claim 3, further comprising estimating the in-plane moment of the rotor blade as a function of at least one of a weight of the rotor blade, a mechanical torque load of the rotor blade, a speed of the rotor blade, a power of the rotor blade, or an inertial load of the rotor blade.

9. The method of claim 8, further comprising calculating the gravity load of the rotor blade as a function of at least one of the rotor azimuth angle, a mass of the rotor blade, gravity, a hub radius, or a center of gravity location of the rotor blade.

10. The method of claim 9, further comprising calculating the mechanical torque load of the rotor blade as a function of at least one of a low-speed shaft torque, a blade radius, or the hub radius.

11. The method of claim 10, further comprising calculating the inertial load of the rotor blade as a function of at least one of a rotor acceleration or a rotor inertia.

12. The method of claim 11, further comprising determining the rotor acceleration based at least partially on a rate of change of a rotor speed signal and filtering the speed signal via a low pass filter.

13. The method of claim 3, further comprising:
estimating an in-plane shear force of the rotor blade as a function of at least one of the rotor azimuth angle, a rotor blade mass, a rotor blade radius, the application point, torque, filtered rotor acceleration, rotor inertia, gravity, aerodynamic drag, wind speed, or a center of gravity location; and calculating the load acting on the rotor blade based at least partially on the in-plane shear force.

14. A system for maintaining rotor blade loads of a wind turbine within predetermined limits while also maximizing power output, the system comprising:
one or more sensors configured to measure a plurality of operating parameters of the wind turbine;
a turbine controller configured with the one or more sensors, the turbine controller comprising a processor configured to perform one or more operations, the one or more operations comprising:
estimating an out-of-plane and in-plane force acting on the rotor blade based at least partially on the plurality of operating parameters;
calculating an application point of the out-of-plane and in-plane force on a span of the rotor blade as a function of a tip-speed ratio and a pitch angle of the rotor blade;
estimating an out-of-plane mom moment of the rotor blade based at least partially on the out-of-plane force and the out-of-plane application point;
estimating an in-plane blade moment of the rotor blade based at least partially on the in-plane force and the in-plane application point;
calculating the load acting on the rotor blade based at least partially on the out-of-plane moment and the in-plane moment; and,
implementing a control action based on the calculated load implementing, the control action comprising at least one of pitching the rotor blade, yawing a nacelle of the wind turbine, derating the wind turbine, uprating e wind turbine, or shutting down the wind turbine.

15. The system of claim 14, wherein the plurality of operating parameters of the wind turbine comprise at least one of the following: a thrust, a power, a speed, a torque, a pitch angle, a nodding moment, an overhang moment, a rotor azimuth angle, or a yawing moment.

16. The system of claim 14, wherein estimating the out-of-plane root moment further comprises;
determining an out-of-plane force distribution from a blade root to a blade tip of the rotor blade; and
integrating the out-of-plane force distribution to obtain an equivalent out-of-plane force.

17. The system of claim 14, wherein determining the application point of the out-of-plane force further comprises:
calculating a plurality of application points of a plurality of out-of-plane forces during operation of the wind turbine, wherein the plurality of application points correspond to a plurality of wind speeds; and
storing the plurality of application points in an aerodynamic performance map.

18. The system of claim 14, wherein the application point of the out-of-plane force comprises a constant value.

19. The system of claim 13, further comprising estimating the in-plane blade root moment of the rotor blade as a function of at least one of a weight of the rotor blade, a mechanical torque load of the rotor blade, a speed of the rotor blade, a power of the rotor blade, or an inertial load of the rotor blade.

20. A method for reducing loads acting on a rotor blade of a wind turbine, the method comprising:
measuring, via one or more sensors, a plurality of operating parameters of the wind turbine;
estimating, via a turbine controller, an out-of-plane force acting on the rotor blade based at least partially on the plurality of operating parameters;

calculating, via the turbine controller, an application point on the rotor blade of the out-of-plane force as a function of a blade radius, a tip-speed ratio and a pitch angle of the rotor blade;

calculating, via the turbine controller, a moment acting on the rotor blade based at least partially on the out-of-plane force and the application point; and, implementing, via the turbine controller, a control action based on the calculated moment, the control action comprising at least one of pitching the rotor blade, yawing a nacelle of the wind turbine, derating the wind turbine, uprating the wind turbine, or shutting down the wind turbine.

* * * * *